(12) United States Patent
Yin et al.

(10) Patent No.: US 9,390,498 B2
(45) Date of Patent: *Jul. 12, 2016

(54) VISUALIZATION AND CHARACTERIZATION OF PULMONARY LOBAR FISSURES

(71) Applicant: VIDA Diagnostics, Inc., Coralville, IA (US)

(72) Inventors: Youbing Yin, Coralville, IA (US); John D. Newell, Jr., Iowa City, IA (US); Philippe Raffy, Edina, MN (US); Susan A. Wood, Palo Alto, CA (US)

(73) Assignee: Vida Diagnostics, Inc., Coralville, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/690,391

(22) Filed: Apr. 18, 2015

(65) Prior Publication Data

US 2015/0294462 A1 Oct. 15, 2015

Related U.S. Application Data

(63) Continuation of application No. 13/804,542, filed on Mar. 14, 2013, now Pat. No. 9,014,445.

(60) Provisional application No. 61/712,700, filed on Oct. 11, 2012.

(51) Int. Cl.
*G06T 7/00* (2006.01)
*A61B 5/08* (2006.01)
*G06T 19/20* (2011.01)
*A61B 6/03* (2006.01)

(52) U.S. Cl.
CPC ............ *G06T 7/0012* (2013.01); *A61B 5/08* (2013.01); *A61B 6/032* (2013.01); *G06T 19/20* (2013.01); *G06T 2200/24* (2013.01); *G06T 2207/10072* (2013.01); *G06T 2207/30061* (2013.01); *G06T 2210/41* (2013.01); *G06T 2219/2012* (2013.01)

(58) Field of Classification Search
None
See application file for complete search history.

(56) References Cited

U.S. PATENT DOCUMENTS

| 7,711,167 | B2 | 5/2010 | Kiraly |
| 2006/0030958 | A1 | 2/2006 | Tschirren et al. |
| 2007/0092864 | A1 | 4/2007 | Reinhardt et al. |

OTHER PUBLICATIONS

Frangi, A. et al., "Multiscale Vessel Enhancement Filtering," MICCAI 1998; 1496 (3), pp. 130-137.

(Continued)

*Primary Examiner* — Siamak Harandi
(74) *Attorney, Agent, or Firm* — Fredrikson & Byron, P.A.

(57) ABSTRACT

Systems and methods for visualizing pulmonary fissures including a processor and software instructions for creating a 3 dimensional model of the fissures. Creating the 3 dimensional model includes accessing volumetric imaging data of the patient's lungs, analyzing the volumetric imaging data to segment the lungs into lobes, using the segmented lobes to identify locations at which pulmonary fissures should be present where the lobes abut each other, analyzing the volumetric images to identify locations at which pulmonary fissures actually are present as existing fissure, comparing the locations at which pulmonary fissures should be present to the locations at which pulmonary fissures are present to identify locations of missing fissure, and creating a visual display comprising a 3 dimensional model of the pulmonary fissures including existing fissure portions and missing fissure portions, with the existing fissure portion visually distinct from the missing fissure portions.

20 Claims, 9 Drawing Sheets

(56) References Cited

OTHER PUBLICATIONS

Li, K. "Efficient Optimal Net Surface Detection for Image Segmentation—From Theory to Practice," M.SC. Thesis, The University of Iowa, Dec. 2003, 68 pages.

Pu, J. et al., "Computerized assessment of pulmonary fissure integrity using high resolution CT," Medical Physics, vol. 37, No. 9, Sep. 2010, pp. 4661-4672.

Tschirren, J. et al., "Intrathoracic airway trees: segmentation and airway morphology analysis from low-dose CT scans," IEEE Transactions on Medical Imaging, vol. 24, No. 12, Dec. 2005, pp. 1529-1539. Abstract and Author manuscript provided.

Tschirren, J. et al., "Matching and Anatomical Labeling of Human Airway Tree," IEEE Transactions on Medical Imaging, vol. 24, No. 12, Dec. 2005, pp. 1540-1547.

Tschirren, J., "Segmentation, anatomical labeling, branchpoint matching, and quantitative analysis of human airway trees in volumetric CT images," Dissertation, The University of Iowa, Aug. 2003, 231 pages.

van Rikxoort, E. et al., "A method for the automatic quantification of the completeness of pulmonary fissures: evaluation in a database of subjects with severe emphysema," European Radiology, vol. 22, pp. 302-309.

"COPD Essentials for Health Professionals," Retrieved from: https://www.nhlbi.nih.gov/health/educational/copd/campaign-materials/html/providercard.htm on Aug. 18, 2014, 2 pages.

Herth, F.J.F. et al., "Endoscopic Lung Volume Reduction," Respiration, vol. 79, No. 1, 2010, pp. 5-13.

Strange, C. et al., "Design of the Endobronchial Valve for Emphysema Palliation Trial (VENT): a non-surgical method of lung volume reduction," BMC Pulmonary Medicine, vol. 7, Jul. 3, 2007, 12 pages.

Riquet, M. et al., "Lung cancer invading the fissure to the adjacent lobe: more a question of spreading mode than a staging problem," European Journal of Cardio-Thoracic Surgery, vol. 41, 2012, pp. 1047-1051.

van Rikxoort, E.M. et al., "Automatic Segmentation of Pulmonary Segments From Volumetric Chest CT Scans," IEEE Transactions on Medical Imaging, vol. 28, No. 4, Apr. 2009, pp. 621-630, Abstract only.

Pu, J. et al., "Pulmonary Lobe Segmentation in CT Examinations Using Implicit Surface Fitting," IEEE Transactions on Medical Imaging, vol. 28, No. 12, Dec. 2009, pp. 1986-1996, Abstract and author manuscript provided.

Ukil, S. et al., "Anatomy-Guided Lung Lobe Segmentation in X-Ray CT Images," IEEE Transactions on Medical Imaging, vol. 28, No. 2, Feb. 2009 pp. 202-214, Abstract only.

Kuhnigk, J-M. et al., "Lung lobe segmentation by anatomy-guided 3D watershed transform," Proceedings of SPIE Medical Imaging, vol. 4, 2003, pp. 1482-1490.

Zhou, X. et al., "Automatic recognition of lung lobes and fissures from multi-slice CT images," Proceedings of SPIE Medical Imaging, vol. 5370, 2004, pp. 1629-1633.

Noppen, Marc, "Collateral Ventilation in End-Stage Emphysema: A Blessing or a Curse for New Bronchoscopic Treatment Approaches (or Both)?" Respiration, vol. 74, No. 5, Jan. 2007, pp. 493-495.

Rodarte, J.R. et al., "Regional lung strain in dogs during deflation from total lung capacity," Journal of Applied Physiology, vol. 85, 1985, pp. 164-172.

Magnussen, H. et al., "Effect of fissure integrity on lung volume reduction using a polymer sealant* in advanced emphysema," Thorax, vol. 67, No. 4, 2012, pp. 302-308.

Sciurba, F.C. et al., "A Randomized Study of Endobronchial Valves for Advanced Emphysema," The New England Journal of Medicine, vol. 363, No. 13, Sep. 23, 2010, pp. 1233-1244.

Sterman, D.H. et al., "A multicenter Pilot Study of a Bronchial Valve for the Treatment of Severe Emphysema," Respiration, vol. 79, No. 3, 2010, pp. 222-233.

Washko G.R. et al., "Physiological and Computed Tomographic Predictors of Outcome from Lung Volume Reduction Surgery," American Journal of Respiratory and Critical Care Medicine, vol. 181, No. 5, 2010, pp. 494-5000.

VISUALIZATION AND CHARACTERIZATION OF PULMONARY LOBAR FISSURES

PRIORITY CLAIM

This application is a continuation of U.S. patent application Ser. No. 13/804,542, filed Mar. 14, 2013, which claims the benefit of U.S. Provisional Application No. 61/712,700, filed Oct. 11, 2012 and entitled Visualization and Characterization of Pulmonary Lobar Fissures, the disclosure of which is hereby incorporated by reference.

FIELD OF THE INVENTION

Embodiments of the invention generally relate to visualization and characterization of pulmonary lobar fissures.

BACKGROUND OF THE INVENTION

Severe emphysema is a debilitating disease that limits quality of life of patients and represents an end state of Chronic Obstructive Pulmonary Disease (COPD). It is believed that 3.5 million people in the US have the severe emphysematous form of COPD, and it is increasing in both prevalence and mortality. Current treatment methods for severe emphysema include lung volume reduction (LVR) surgery, which is highly invasive, and can be risky and uncomfortable for the patient. New treatment methods for treating emphysema include bronchoscopy guided LVR (BLVR) devices such as one-way valves that aim to close off ventilation to the diseased regions of the lung, but maintain ventilation to healthier lung. Bronchoscopy-guided techniques have the promise to be less invasive, less costly and more highly accurate treatments for patients with severe disease and improve the quality of life of severe emphysema patients.

Emphysema can present itself in various disease forms (i.e., phenotypes). Predicting the right treatment for these patients at the appropriate time in the disease process likely depends on the phenotype of the disease. Imaging techniques provide an in-vivo mechanism to objectively quantify and characterize disease phenotypes and can be used in the patient selection process for the various procedural options. Quantitative imaging biomarkers can be used to effectively phenotype disease and therefore predict those patients most likely to respond to the targeted treatment options. By triaging patients to the appropriate therapy, there exists a greater promise for a positive impact on patient outcome, reduced healthcare costs, and replacing more invasive procedures like LVR surgery in treating patients with severe emphysema.

Fissures are important anatomical structures within lungs. It is believed that fissures have an effect on regional lung mechanics. For example, adjacent lobes can slide against each other at fissure interfaces, which provide a means to reduce lung parenchymal distortion. In addition, intact fissures play an important role in reducing collateral ventilation among lobes and the spread of diseases. Recently, fissure integrity has emerged as a strong biomarker to predict the response to interventional emphysema therapies including localized lung volume reduction. In short, if the fissure of the lung is intact, an obstructive device like a valve will more likely produce a seal leading to the atelectasis (i.e., collapse) of the diseased lung sub-region. Without an intact fissure, there is a possibility of collateral ventilation and the likelihood of success of the procedure may be reduced. However, accurately detecting and characterizing fissures in diseased lungs is difficult.

Methods of detecting fissures include fitting the existing portions of the fissures to a lobar atlas (as described in E. M. van Rikxoort et al., "A method for the automatic quantification of the completeness of pulmonary fissures: evaluation in a database of subjects with severe emphysema," European radiology, (2011): 0-7, for example) or by an extrapolation of the existing portion of the fissure to the absent portion (as described in J. Pu et al., "Computerized assessment of pulmonary fissure integrity using high resolution CT.," Medical Physics, 37(9), (2010): 4661-4672, for example). However, neither of these approaches makes full use of the anatomic information available in the image data.

SUMMARY

Certain embodiments of the present invention are described in the following illustrative embodiments.

Embodiments of the invention automatically detect, display and/or characterize fissures in diseased lungs such that the fissures may function as a biomarker that is predictive of patients' response to a procedure for treatment of emphysema and other diseases.

Some embodiments include a system for visualizing pulmonary fissures of a patient's lungs including a processor and software comprising instructions for the processor for creating a visual display comprising the 3 dimensional model of the pulmonary fissures. Creating a visual display comprising a 3 dimensional model of the pulmonary fissures may include accessing volumetric imaging data of the patient's lungs, analyzing the volumetric imaging data to segment the lungs into lobes, using the segmented lobes, identifying locations at which pulmonary fissures should be present as the locations where the lobes abut each other, analyzing the volumetric images to identify locations at which pulmonary fissures are present as existing fissure, comparing the identified locations at which pulmonary fissures should be present to the identified locations at which pulmonary fissures are present to identify locations of missing fissure, and creating a visual display comprising a 3 dimensional model of the pulmonary fissures comprising existing fissure portions and missing fissure portions, wherein the existing fissure portion are visually distinct from the missing fissure portions. In some embodiments, the existing fissure portions may be displayed in a different color than the missing fissure portions in the 3 dimensional model.

In some embodiments, the software further includes instructions to create a graphical user interface allowing a user to reclassify a location on the 3-dimension model of the fissure from existing to missing or from missing to existing by interacting with the 3 dimensional model on the graphical user interface.

In some embodiments, the 3 dimensional model of the fissures also includes a 3 dimensional representation of the lung parenchyma in combination with the fissures. In some embodiments, the 3 dimensional model of the fissures may also include a 3 dimensional representation of a tumor in combination with the fissures, and the software may further include instructions for identifying a location of the tumor by analyzing the volumetric imaging data. For example, the software may include instructions to calculate a distance between the tumor and a nearest fissure location. 13. In some embodiments, the software further includes instructions for calculating the thickness of an existing fissure.

In some embodiments, the software further includes instructions for calculating a numerical value representing integrity of the fissures. The numerical value may provide a relative proportion of amount of the fissure that exists and amount of fissure that is missing. In some embodiments, the software may include instructions for calculating a numerical value representing integrity of a portion of a fissure abutting a lobe, wherein the portion of the fissure abutting the lobe is less than the complete fissure. In some embodiments, the software may further include instructions for calculating a numerical value representing integrity of a portion of a fissure abutting a sub-lobe.

In some embodiments, the software may further include instructions for receiving directions from a user to reclassify a fissure location identified by the system as existing fissure to be identified and displayed as missing fissure in the 3 dimensional model. Alternatively or additionally, in some embodiments, the software may further include instructions for receiving directions from a user to reclassify a fissure location identified by the system as missing fissure to be identified and displayed as existing fissure in the 3 dimensional model.

Other embodiments include a system for visualizing pulmonary fissures of a patient's lungs including a processor and software including instructions for the processor for creating a visual display comprising the 3 dimensional model of the pulmonary fissures. Creating a visual display including a 3 dimensional model of the pulmonary fissures may include accessing volumetric imaging data of the patient's lungs, analyzing the volumetric imaging data to segment the lungs into lobes and sub-lobes, using the segmented lobes to identify locations at which pulmonary fissures should be present where the lobes abut each other, analyzing the volumetric images to identify locations at which pulmonary fissures are present, comparing the identified locations at which pulmonary fissures should be present to the identified locations at which pulmonary fissures are present to identify locations of missing fissure, identifying portions of the present and missing fissures which abut the sub-lobes, and creating a visual display comprising a 3 dimensional model of the pulmonary fissures comprising existing fissure portions and missing fissure portions in which the existing fissure portion are visually distinct from the missing fissure portions and in which the portions of the missing and existing fissures abutting the sub-lobes are visually distinct from each other. For example, the existing fissure portions may be displayed in a different color than the missing fissure portions in the 3 dimensional model. In some embodiments, the missing and existing fissures abutting the sub-lobes are each presented in a different color.

In some embodiments, the software further includes instructions for calculating a numerical value representing integrity of the fissures, in which the numerical value provides a relative proportion of amount of the fissures that exists and amount of fissure that is missing. For example, the numerical value representing integrity of the fissures may be a calculation of the integrity of an entire fissure, of only a portion of a fissure which is less than the whole fissure abutting a lobe, or only a portion abutting a sub-lobe, wherein selection of the entire fissure, the portion abutting the lobe, or the portion abutting a sub-lobe can be determined by a user.

In some embodiments, the software further includes instructions for receiving directions from a user interacting with the 3 dimensional model of the fissures on a graphical user interface to reclassify a fissure location identified by the system as existing fissure to be identified and displayed as missing fissure, and to reclassify a fissure location identified by the system as missing fissure to be identified and displayed as existing fissure.

Other embodiments include methods of creating a three dimensional model of pulmonary fissures of a patient including accessing volumetric imaging data of the patient's lungs, analyzing the volumetric imaging data to segment the lungs into lobes, using the segmented lobes to identify locations at which pulmonary fissures should be present as the locations where the lobes abut each other, analyzing the volumetric images to identify locations at which pulmonary fissures are present as existing fissure, comparing the identified locations at which pulmonary fissures should be present to the identified locations at which pulmonary fissures are present to identify locations of missing fissure, and displaying the three dimensional model on a display, in which the visual display includes existing fissure portions and missing fissure portions and in which the existing fissure portion are visually distinct from the missing fissure portions.

Using objective, quantitative measures of disease obtained from imaging modalities like computerized tomography (CT) in routine clinical practice requires providing accurate and immediate information to a physician in a busy practice. Anatomic structural deformities in lung fissure can be more easily understood within a visual context. Embodiments of the invention therefore provide easy and immediate access to pertinent measures of disease and enhanced multidimensional visual models, for easy consumption by the clinician such as the pulmonary physician.

BRIEF DESCRIPTION OF THE DRAWINGS

The following drawings are illustrative of particular embodiments of the invention and therefore do not limit the scope of the invention. The drawings are not necessarily to scale (unless so stated) and are intended for use with the explanations in the following detailed description. Embodiments of the invention will hereinafter be described in conjunction with the appended drawings, wherein like numerals denote like elements.

DETAILED DESCRIPTION

Figure 1:
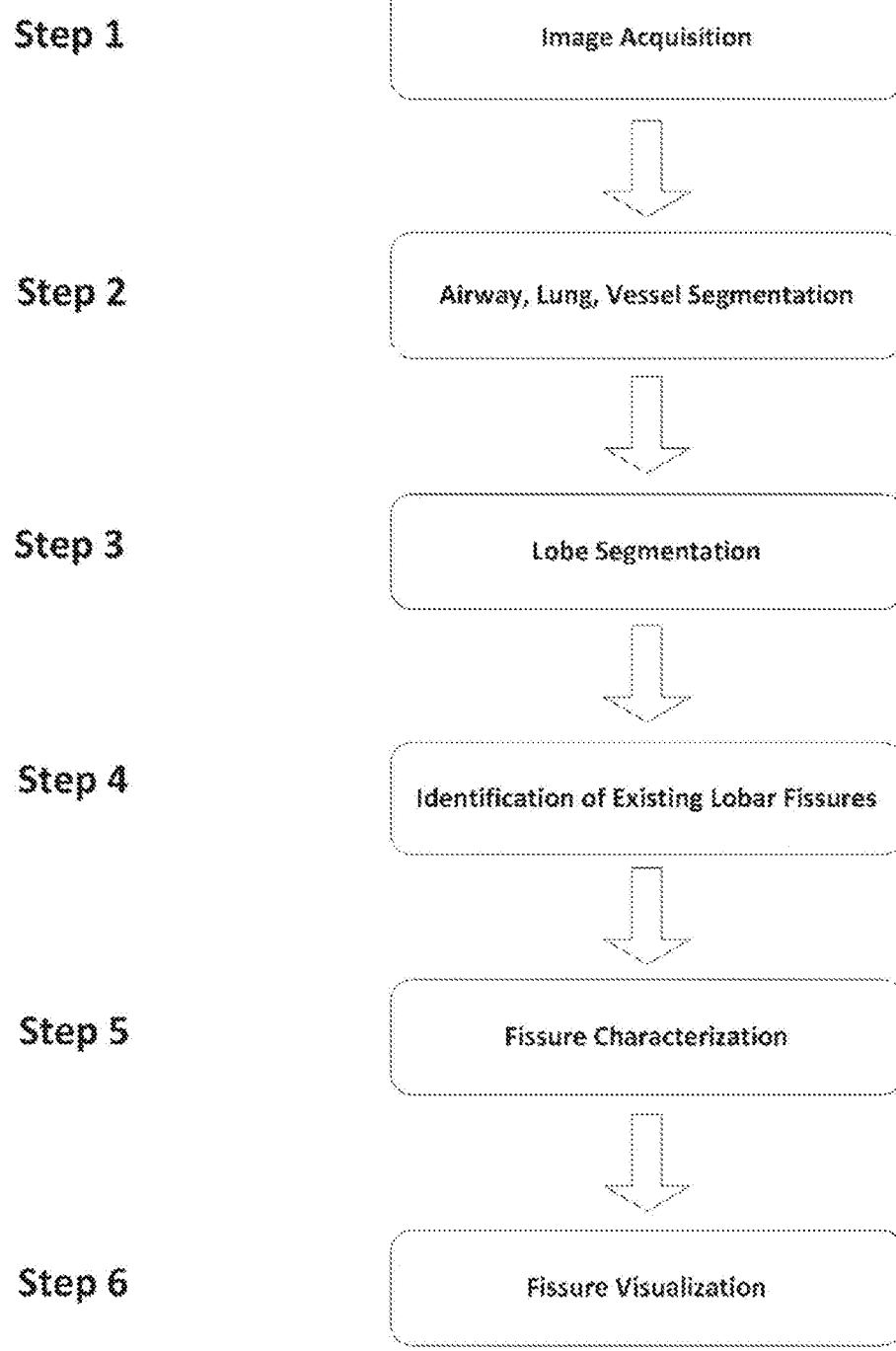
FIG. 1 shows a flowchart of a fissure characterization and visualization method associated with certain embodiments of the invention.

The invention describes a process to automate, display, interact with and characterize the fissures of the lung in multiple dimensions. When the human lung is imaged in vivo with an imaging acquisition device, like CT, that image can be reconstructed and evaluated to depict normal and diseased states. Because of the various subclasses of disease and the various depictions (phenotypes) of a disease entity, evaluation of lobular regions of the lung and the fissures separating them are important to accurately characterize disease and predict response to BLVR therapy.

This disclosure includes methods to provide visualization of the fissures in two and three dimensions, define the fissure boundaries, characterize their morphologic characteristics which may be used for identifying a disease phenotype, and visualize regions of intact and missing fissures, and observe the difference between normal and diseased lung in an instantaneous and automated way to enable clinical decision making.

The left and right lungs are each divided into a plurality of lobes by deep clefts, which are the interlobar fissures, referred to herein simply as fissures. The outer surface of the lungs is lined by pleura, including an inner layer which is the visceral pleura which dips into the fissures to surround the lobes. The fissures therefore are the join between the lobes of the lung and are defined by the outermost surface of the lobes and the visceral pleura at the locations where the lobes abut each other. Therefore, although the fissure itself is actually an interface between abutting lobes, it is the very thin layer of the lobar interfaces that can be detected on a volumetric image and is interpreted as being the fissure. The right lung normally includes three lobes (the upper, middle, and lower lobes) which are divided by two fissures, known as the oblique and the horizontal fissure. The left lung normally includes two lobes (the upper and lower lobes) with one fissure, the oblique fissure, between them.

The edges of the lobes and the pleura that lines the lobes define the fissures and separate the lobes such that the ventilation of each lobe separates from that of adjacent abutting lobes. In addition, the pleura normally form a smooth surface, allowing abutting lobes to slide relative to each other during inhalation and exhalation. However, in certain disease conditions, the pleura may become thickened or adherent. In addition, abutting lobes may adhere to each other and the pleura and lung margins that normally define the fissure may be lost. In such locations, the fissure is described as "incomplete," "missing," or "absent" and air can flow between the lobes. Various embodiments described herein identify the fissures using volumetric radiological images such as CT and present them visually in 2D images or in 3D models for a user such as a clinician. In some embodiments, the absent portions of the fissures are also identified and can also be visualized, as by showing the "absent" portions in a color which is distinct from the existing fissures, in a location in which they would normally be present in a complete fissure.

Various embodiments may be performed by a lung visualization system, which may include a processor, such as a processor in a computer, and may also include a visual display such as a monitor or screen. The system may also include instructions included in software (computer readable media), stored in memory of the system, and operable on the processor. The software may include instructions for the processor to perform the various steps and methods described herein, including instructions to receive patient data including volumetric imaging data, analyze the data to characterize the fissures, and display images including three-dimensional images of the fissures resulting from the analysis of the imaging data on the visual display. The software may be incorporated into 3D pulmonary imaging software.

It should also be understood that the three-dimensional images or models described herein are not truly created in three dimensions, because they exist on a flat two-dimensional visual display. Rather, the three-dimensional images described herein use perspective and shading, with the closest portions depicted in the foreground and more distant portions in the background, along with the ability of the user to rotate the images in some cases and/or to see multiple views, to show the entire volumetric volume on the visual display. In contrast, each image in the series of the multi-dimensional volumetric images provided by CT and MRI scans, for example, is a two-dimensional planar image that depicts the tissue present in a single plane or slice. These images are typically acquired in three orthogonal planes, which are referred to as the three orthogonal views and are typically identified as being axial, coronal and sagittal views.

Embodiments of the invention allow the clinician to interact with the three-dimensional model of the lungs and the two-dimensional volumetric images associated with and used to generate the model. For example, the three-dimensional model and the associated two-dimensional volumetric images may be presented in a graphical user interface on a visual display. The user may interact with the graphical user interface, such as by selecting a button, icon, and/or one or more locations on the images or the model or elsewhere using a mouse, stylus, keypad, touchscreen or other type of interface known to those of skill in the art. The creation of the three-dimensional model may be performed by the system including a processor with software (computer readable media) to perform this function as well as software to permit a user to interact with the graphical user interface, to calculate and display desired data and images, and to perform the other functions described herein. The system may further include the visual display on which the graphical user interface is displayed. The three-dimensional model and two-dimensional volumetric images may be provided to a user (such as a clinician or researcher) as a graphical user interface on a visual display, which may be a computer screen, on which the images and data may be manipulated by the user.

Examples of the embodiments may be implemented using a combination of hardware, firmware, and/or software. For example, in many cases some or all of the functionality provided by examples may be implemented in executable software instructions capable of being carried on a programmable computer processor. Likewise, some examples of the invention include a computer-readable storage device on which such executable software instructions are stored. In certain examples, the system processor itself may contain instructions to perform one or more tasks. System processing capabilities are not limited to any specific configuration and those skilled in the art will appreciate that the teachings provided herein may be implemented in a number of different manners.

FIG. 1 shows a flowchart of a fissure characterization and visualization method which may be carried out using software as part of a pulmonary imaging system, for example. At step 1, volumetric radiological images or imaging data of a patient are transmitted to the pulmonary imaging system. Alternatively, the volumetric radiological images or imaging data may already be stored within the memory of the system and may be accessed by the processor. The volumetric radiological images or imaging data may be CT scans, MRI scans, and/or PET scans, for example, from which a series of two-dimensional planar images (referred to herein as two-dimensional volumetric images or two-dimensional images) can be produced in multiple planes, for example.

At step 2, the lungs, airways, and/or blood vessels are segmented using the 3D image data. The methods of performing lung, airway and vessel segmentation from the volumetric images or imaging data may be those employed by the Pulmonary Workstation of Vida Diagnostics, Inc. (Coralville, Iowa) and as described in the following references, each of which is incorporated herein by reference: United States Patent Publication 2007/0092864, which is entitled: Treatment Planning Methods, Devices and Systems; United States Patent Publication 2006/0030958, which is entitled: Methods and Devices for Labeling and/or Matching; Tschirren et al., "Intrathoracic airway trees: segmentation and airway morphology analysis from low-dose CT scans," IEEE Trans Med Imaging. 2005 December; 24 (12):1529-39; Tschirren et al., "Matching and anatomical labeling of human airway tree," IEEE Trans Med Imaging. 2005 December; 24 (12):1540-7; Tschirren, Juerg, "Segmentation, Anatomical Labeling, Branchpoint Matching, and Quantitative Analysis of Human Airway Trees in Volumetric CT Images," Ph.D. Thesis, The University of Iowa, 2003; Tschirren, Juerg, Segmentation, Anatomical Labeling, Branchpoint Matching, and Quantitative Analysis of Human Airway Trees in Volumetric CT Images, Slides from Ph.D. defense, The University of Iowa, 2003; and Li, Kang, "Efficient Optimal Net Surface Detection for Image Segmentation—From Theory to Practice," M.Sc. Thesis, The University of Iowa, 2003, for example. Segmentation of the lungs, airways, and vessels results in identification of the lungs, airways, and vessels as distinct from the surrounding tissues and of separation of the lungs, airways, and vessels into smaller distinct portions which may be individually identified in accordance with standard pulmonary anatomy.

At step 3, lobar segmentation is performed. The segmentation of the lungs, airways, and vessels obtained in step 2 can be used to identify and delineate the lobes, again by applying standard pulmonary anatomy. For example, using the identified segments of the airway and/or vessel trees obtained in step 2, the lobes may be segmented and identified by extracting the portions of the airway tree corresponding to particular lobes based on known airway tree structures and connectivity information. The extracted lobar airway tree portions may be further divided into portions corresponding to sub-lobes, again based on known airway and/or vessel tree structure and connectivity information. In this way, the portions of the volumetric images corresponding to lobes and/or sub-lobes can be identified.

Figure 2:
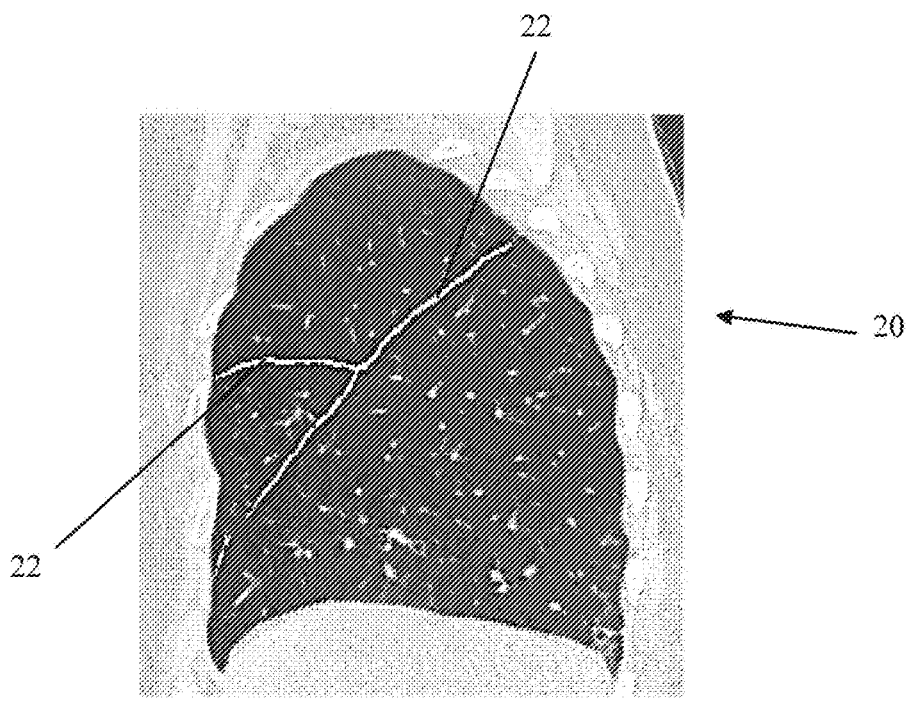
FIG. 2 shows a CT scan in a sagittal view in which the fissures have been enhanced.

In step 4, the lobar fissures portions of the volumetric images are identified by the system. The lobar fissures, as formed by the abutting pleural lining of the lobes, can be seen radiologically on X-ray as well as on two-dimensional, volumetric images such as CT scans. As revealed by the tissues lining the fissures. The fissures may be automatically detected by the system in the volumetric images using known methods or other methods. In some embodiments, identification of the lobar fissures begins with enhancing the fissures to ensure accurate detection. In some embodiments, Hessian-matrix or structure tensor based approaches may be used for identification and enhancement of the fissures, as described in A. F. et al., "Multiscale vessel enhancement filtering," MICCAI. 1998; 1496 (3):130-7, for example. The identified fissures may be enhanced and shown to the user on the volumetric image. An example of this is shown in FIG. 2, which is a sagittal CT scan 10 including enhanced fissure lines 12.

In step 5, the fissures may be characterized. This may be accomplished by combining the information about the lobar segmentation obtained in step 3 with the fissure identification obtained in step 4. The locations at which the lobar regions abut each other may be used to identify the location where a fissure would normally be present. However, in some individuals, portions of the fissure (the tissue lining the fissure) may be absent. Therefore, the normal fissure locations as determined from the lobar anatomy can be compared to the actual fissure locations identified in step 4. If there is a location where a fissure would normally be present as determined by the abutting lobe surfaces, but the fissure identification indicated that there was no fissure present in a portion of or all of that location, then the fissure is described as missing, absent or incomplete in that location. In this way, the pulmonary imaging system not only can identify and highlight existing fissures for users and present them in two-dimensional images and three-dimensional models, but can also identify locations where the fissure is absent. The extent and location of absent fissures can then be used to characterize the patient's disease and to determine appropriate therapeutic approaches. This method differs from existing methods in which absent portions are calculated by either fitting the existing portions of the fissures to a reference atlas (van Rikxoort et al, 2011) or by an extrapolation of the existing portion of the fissure to the absent portion (Pu, et al., 2010). In the lobar atlas approach, a reference atlas is created using the fissure locations of a group of subjects. The fissures of an individual patient can be compared to the reference atlas to predict the locations of absent portions of the fissures. This method relies on consistency of anatomy among individuals, which may not be accurate, particularly in the presence of severe disease which can dramatically change fissure patterns. In the extrapolation based method, the location of missing fissures is estimated by extending existing fissures into the missing spaces. This method may cause unpredictable errors, particularly in patients having low fissure completeness. Therefore, although these and other alternative methods of identifying missing fissures may be used, these other approaches do not make full use of the anatomic information available in the CT image data in the way that the identification of abutting fissures does.

Once the locations of existing fissures and absent fissures have been identified, they can be presented visually to a user in two dimensions, such as on a CT scan, or in three dimensions, such as in a three-dimensional model. This step of fissure visualization is indicated at step 6 on FIG. 1. In some embodiments, the visual presentations can either show only the existing fissures, with gaps where the fissures are absent. In other embodiments, only the areas of missing fissure may be shown. In still other embodiments, the areas of missing fissures can be shown, with the missing fissure being shown as the way the fissure would look if it were present. In some embodiments, the missing fissure is shown in a way that contrasts with the existing fissure, to clearly indicate that, although a fissure is shown, the displayed fissure actually represents an area of missing fissure. For example, the missing fissure portions may be shown in a different color than the existing fissure portions. The fissures may be shown as a three-dimensional model in isolation or in combination with other components of the lungs such as the airway tree, parenchyma, and/or the vessels.

Figure 3:
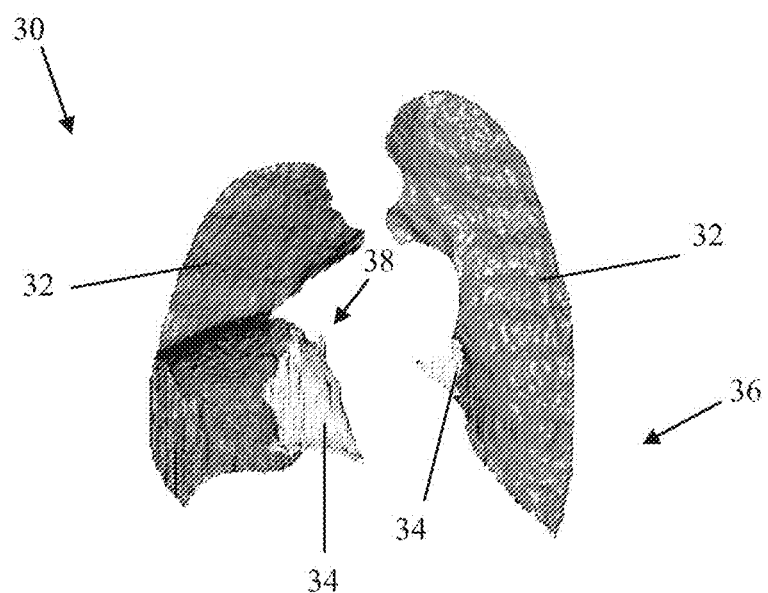
FIG. 3 shows three-dimensional models of surface rendering of fissures of an emphysema patient in accordance with certain embodiments of the invention.

An example of a three-dimensional model of a patient's fissures 30 in isolation is shown in FIG. 3, with the existing fissure portions 32 shown in a first color represented by dark gray and the missing fissure portions 34 shown in a second color represented by light gray. In this patient, who suffers from emphysema, the left oblique fissure 36 is more than 95% complete, while the horizontal fissure 38 is only about 70% complete.

Figure 4A:
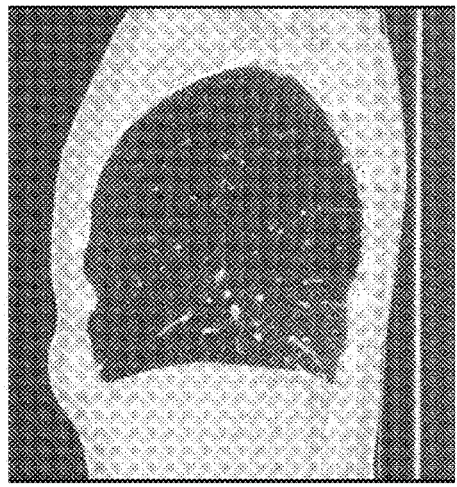
FIG. 4a shows an example of a sagittal CT image of the right lung without fissures identified and highlighted in accordance with certain embodiments of the invention.
Figure 4B:
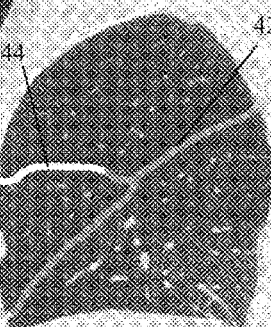
FIG. 4b shows an example of a sagittal CT image of the right lung with fissures identified and highlighted in accordance with certain embodiments of the invention.

In FIG. 4b, the existing 42 and missing portions 42, 44 of a patient's fissures are shown in two dimensions, overlaid on a sagittal view CT image 20 of the right lung of a patient. The existing fissures 42 are shown in a first color represented by dark gray, while the missing portions 44 are shown in a second color represented by white. For purposes of comparison, the same CT image is shown in FIG. 4a without the fissure overlay. It can be appreciated how much more difficult it is to determine the location of the fissures, and what portions are absent, without the assistance of the fissure visualization provided in FIG. 4b.

Figure 5:
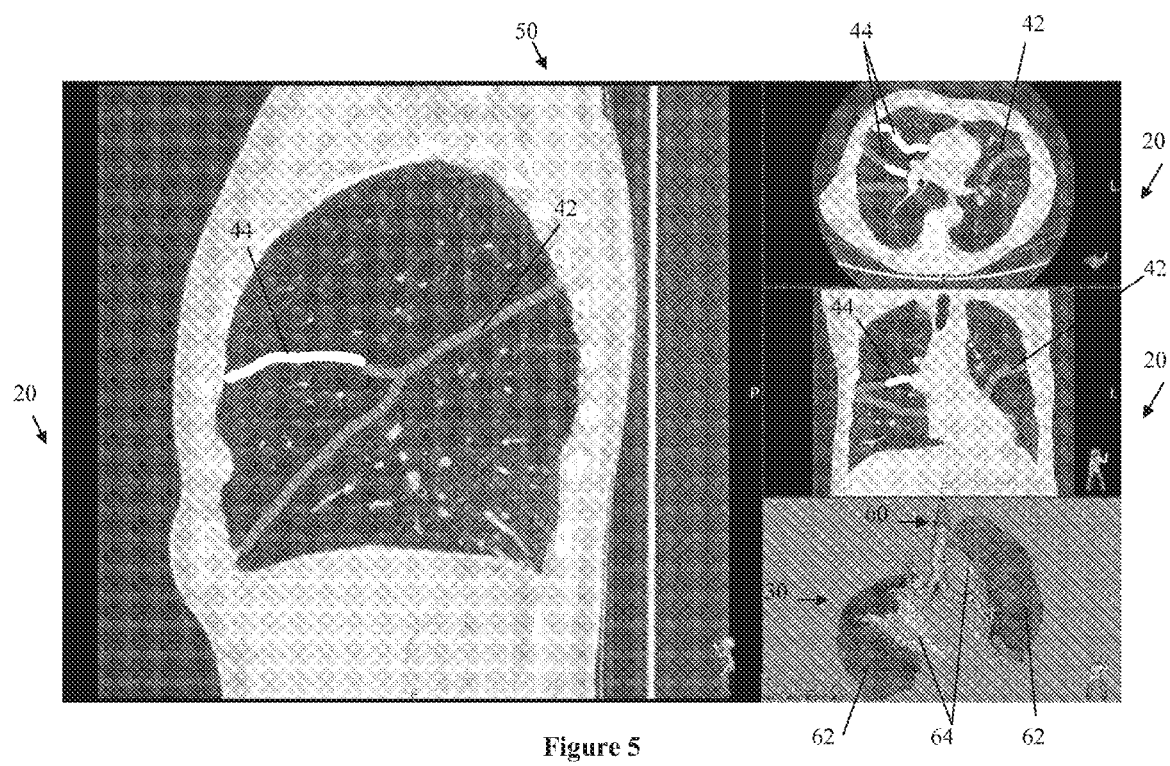
FIG. 5 shows an example of a screen shot including highlighting of the fissures in various two-dimensional CT images and a corresponding three-dimensional volume rendering in accordance with certain embodiments of the invention.

FIG. 5 is an example of fissure visualization in multiple views, as it may be presented to a user in a graphical user interface and therefore represents a screen shot 50 that may be provided by the pulmonary imaging system. It can be seen that the screenshot 50 includes CT images 20 in the three orthogonal views: a sagittal view, an axial view, and a transverse view. In each of the CT images 20, the existing and missing portions of the fissures 42, 44 are enhanced using a different color, with a first color represented by dark gray indicating the existing fissure 42 and a second color represented by white indicating the missing fissure 44. The user may have the option to select different images to be presented on the display, such as by moving from one image to another in a series for a particular view. The screenshot 50 also includes a three-dimensional model of the fissures 30 along with a model of the airway tree 60, constructed from the analysis of the two-dimensional volumetric data, with the areas existing and missing fissures 62, 64 shown in different colors corresponding to the colors used in the two dimensional images and represented by dark gray and light gray for purposes of visualization in this figure.

In addition to using the fissure information to visually enhance or display the fissures, the fissure information can also be used to characterize the fissures, as indicated at step 5 of FIG. 1. Such fissure characterization can include characterizing the location of disease, disease heterogeneity, and/or extent of disease (such as the Global Initiative for Chronic Lung Disease, or GOLD, classification system), for example.

In some embodiments, a fissure integrity score may be calculated to characterize the fissure of a portion thereof. The fissure integrity score may be calculated as the incompleteness percentage (IP) or conversely as the completeness percentage (CP). These values may be calculated using the total area of existing fissure and of the absent fissure portions determined as described above using the following equations:

$$IP(\%) = 100 * [1 - ExistingFissure/(ExistingFissure + AbsentFissure)]$$

$$CP(\%) = 100 * ExistingFissure/(ExistingFissure + AbsentFissure)$$

These measurements can be made for a single fissure, for a selected portion of a fissure such as only a portion abutting a particular lobe or sub-lobe, or for a combination of fissures or selected portions of fissures. The choice of which portion of the fissure to assess may be determined by the possible locations of therapeutic interventions such as BLVR surgery. That is, the fissure integrity score may be calculated for those fissures or portions thereof which abut a lobe or sub-lobe for which BLVR therapy is being considered. For example, if bronchoscopy guided BLVR therapy is being considered for either the left upper lobe or the left lower lobe, the fissure integrity score may be calculated for the entire left oblique fissure, because this fissure abuts both of these lobes along its entire length. If the use of BLVR therapy is being considered in the right lower lobe, the fissure integrity score may be calculated based on the entire right oblique fissure. If BLVR surgery is being considered for the right upper lobe, the fissure integrity score may be calculated from the combination of the upper part of the oblique fissure (only the portion of the fissure abutting the right upper lobe) and the entire horizontal fissure. If BLVR surgery is being considered for the right middle lobe, the fissure integrity score may be calculated for a combination of the lower part of the oblique fissure (only the portion of the fissure abutting the right middle lobe) and the entire horizontal fissure.

Because the fissure integrity score provides a numerical assessment of how intact (or not intact) the fissures are, it provides a global quantitative assessment of possible collateral ventilation. For example, if the completeness percentage is 100%, the fissure is intact and there is likely no collateral ventilation between adjacent lobes. BLVR therapy is therefore more likely to be successful. On the other hand, of the fissure integrity score indicates that the fissure completeness is low, collateral ventilation may occur through the missing areas of fissure and the outcome of BLVR therapy may be less successful.

In some embodiments, the fissure integrity score may be used to decide whether or not to proceed with BLVR therapy and in which lobes or sub-lobes to perform such therapy. For example, a fissure integrity score cut-off or threshold may be used for therapeutic decision making A patient with a completeness percentage below the threshold may be ineligible for BLVR surgery for the corresponding portion of the lung. Likewise a patient with an incompleteness percentage above the threshold may be ineligible for BLVR surgery for the corresponding portion of the lung. The fissure integrity score may therefore be used to triage patients as being ineligible for, or possibly eligible for, BLVR therapy.

In some embodiments, the relationship between the existing and absent fissures and other normal or abnormal lung structures can also be evaluated and measured. For example, the lobes of the human lungs can be further dived into bronchopulmonary segments, also called sub-lobes. Each sub-lobe is supplied by one bronchus. There are typically 10 sub-lobes in the right lung (3 in upper lobe, 2 in middle lobe, 5 in lower lobe) and 8-10 sub-lobes in the left lung (4-5 in upper lobe, 4-5 in lower lobe). Depending on their locations, the surfaces of some sub-lobes may be located at fissure locations, thus contacting the fissures at such locations, or they may not abut the fissures. In some embodiments, the portion of a fissure contacting a sub-lobe may be identified and characterized as separate from the remainder of the fissure. For example, characterization of a fissure in a sub-lobe contacting area can be performed (such as the completeness percent or the incompleteness percent) and the portions of fissures in contact with different sub-lobes can be visually distinguished from each other when displayed for user.

Figure 6:
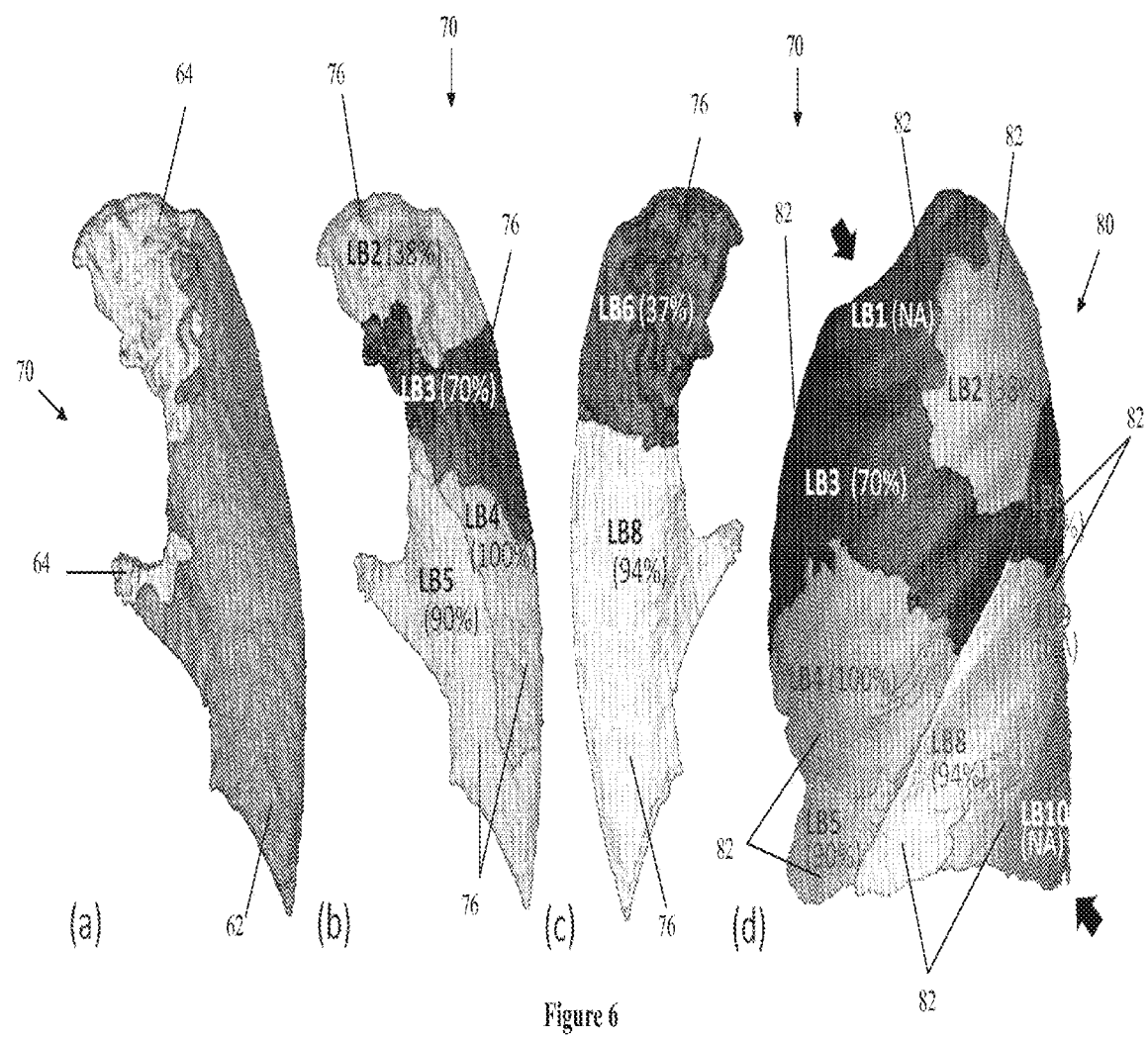
FIG. 6 shows an example of three-dimensional models of a fissure (a)-(c) and of the sublobes surrounding the fissure (d).

A visual presentation of the portions of fissures which contact various sub-lobes can be provided to clinicians as an indication of the fissure integrity at a sub-lobar level. An example of this is shown in FIGS. 6 (a)-(d) in which 3 dimensional models of portions of a fissure are shown in a variety of ways that such models may be provided to a clinician, with the sub-lobe labels having been identified and displayed with the fissure portions based on the sub-lobe associated with (contacting) that portion of the fissure. In these figures, the portions of the fissures contacting different sub-lobes are each colored differently, represented by different shades of gray in the figures, in order to distinguish them from each other, and different colors are also used to distinguish existing from missing fissure portions. In FIG. 9(a) the existing portions 62 left oblique fissure 70 are shown in dark gray while the absent portions 64 shown in light gray. In FIG. 6(b), the left oblique fissure 70 is again shown, with each area of contact of the sub-lobes 76 of the left upper lobe with the fissure distinctly colored and labeled. Similarly, in FIG. 6(c), the left oblique fissure is shown (as seen from below, the opposite side as shown in FIG. 6(b)) with each area of contact of the sub-lobes 78 of the left lower lobe distinctly colored and labeled. In FIG. 6(d), the entire left lung is shown as a three-dimensional model 83, with each of the sub-lobes 82 separately and distinctly colored (shown in shades of gray) and labeled with a sub-lobe label 84 and with the fissure completeness score 86 for each portion of the fissure in contact with that sub-lobe.

This information relating to the completeness percentage of the portion of a fissure contacting a sub-lobe may be used in combination with other information, such as density based emphysema measurements, which may be specific to the lobes or sub-lobes, for example, to guide BLVR treatment planning. This sub-lobe fissure information can then be used as a degree of the influence of fissure integrity on sub-lobes. If treatment is being planned for a particular lung volume such as a lobe or sub-lobe, and if a portion of the fissure contact with that lung volume has a low fissure integrity, the treatment of that lung volume may not be effective or may be less effective than desired due to collateral ventilation from across the fissure. In such cases, the treatment plan may be modified to manage the portion of the fissure having low fissure integrity. For example, the treatment plan may include targeted treatment of the particular lung volume as well as a sub-lobe or sub-lobes on the contralateral side of the fissure from the particular lung volume and adjacent to the portion of the fissure having low fissure integrity. In this way, collateral ventilation of the particular treated lung volume can be prevented by targeted treatments to lung lobes or sublobes across from each other on both sides of a portion of the fissure having low fissure integrity.

Other useful information which can be determined based on the fissure identification includes the spatial relationship between fissure locations and the regions of the lung affected by emphysema, for example. For example, the distance of fissures (both intact and missing portions) from the centroids of regions of emphysema can be calculated. The orientation of the fissures relative to the regions of emphysema can also be determined. This distance and orientation information can be used to predict the impact of fissure integrity on treatments in the corresponding regions of emphysema. Additionally, the information may help with characterizing the emphysema and understanding the impact of fissure integrity on the progress of the emphysema.

Figure 7:
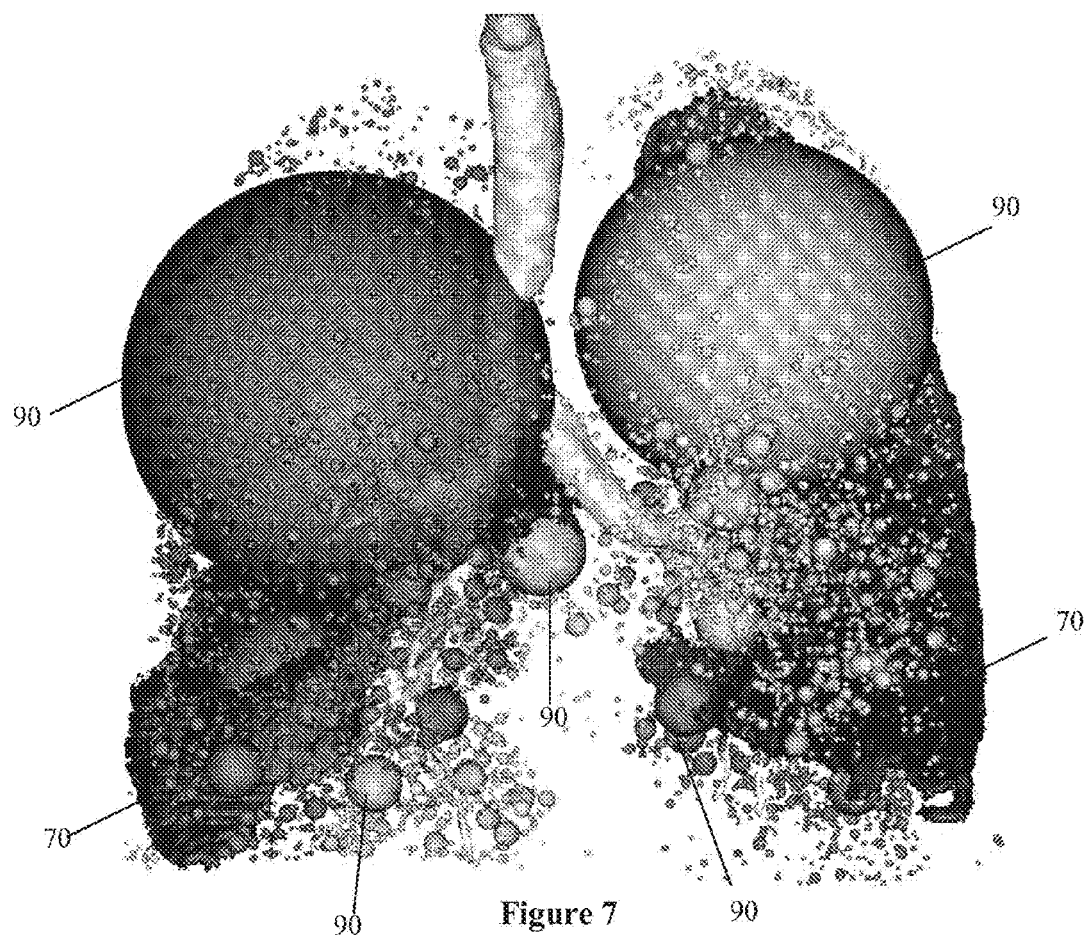
FIG. 7 shows an example of visualization of the spatial relationship between fissures and regions of emphysema in a three-dimensional model in accordance with certain embodiments of the invention.

FIG. 7 is an example of a visual representation of the spatial relationship between fissures 70 and regions of emphysema as it may be provided to a clinician in various embodiments. The visual representation can be used by the clinician to visually assess the local influence of emphysema on fissure integrity. In FIG. 7, the regions of emphysema are symbolically represented by spheres 90 with radii reflecting the sizes of those regions, though other types of visual representations may alternatively be used.

Figure 8:
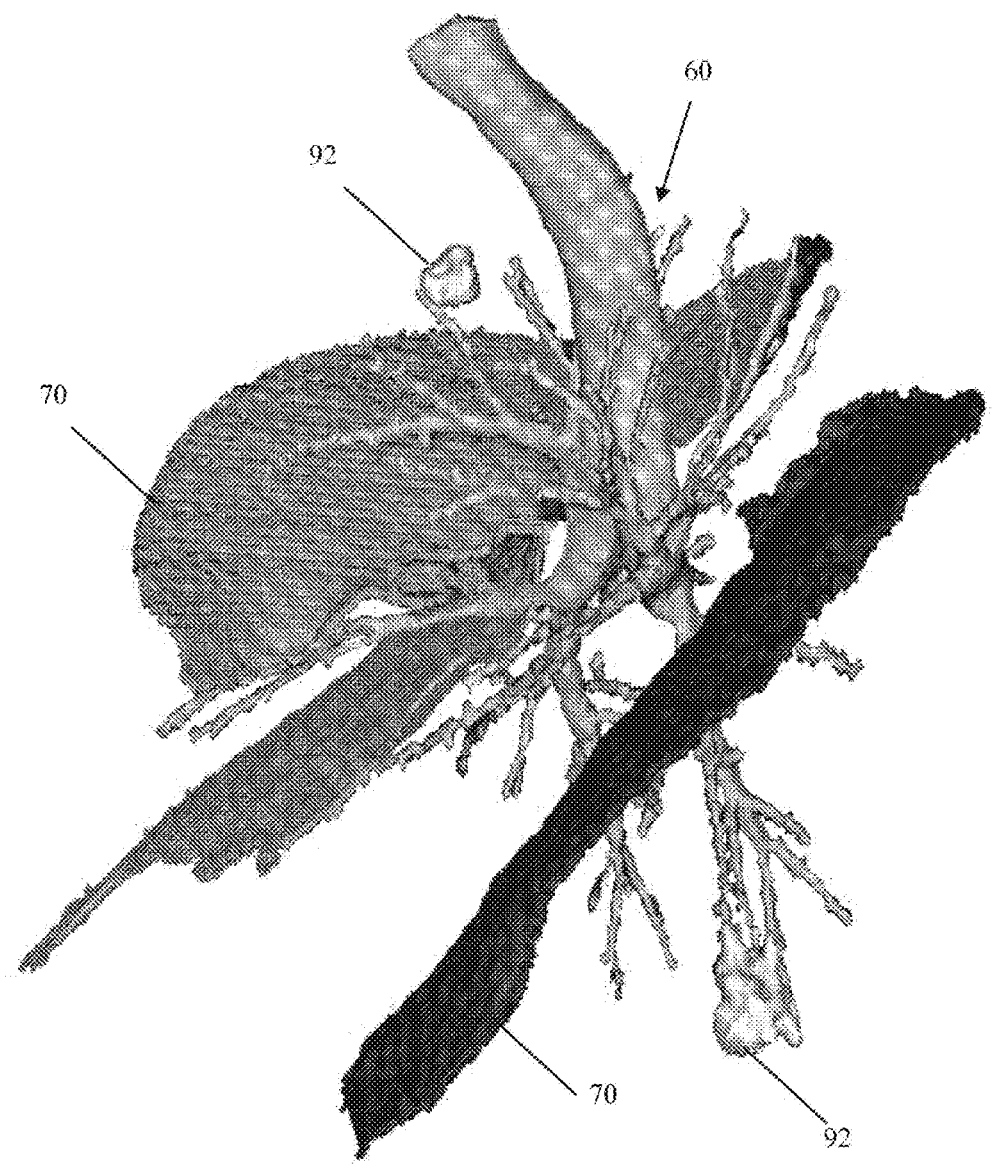
FIG. 8 shows an example of visualization of the spatial relationship between fissures and tumors in a three-dimensional model in accordance with certain embodiments of the invention.

Other information which can be determined using the fissure identification includes the spacial relationship between fissures and tumors, which may have an impact on patient prognosis. For example, recent findings suggest that the presence of tumor invasion through a fissure has a significant negative impact on long-term survival, due perhaps to the rapid spread of such tumors. Thus, it is useful to know the relative locations of fissures and tumors, the distance between them, and whether or not the tumors invade the fissures. Various embodiments therefore identify the locations of tumors and fissures, provide images such as the 3 dimensional model of the fissures 70 and airways tree 60 shown in FIG. 8 in which the tumor 92, fissures 70, and the airway tree 60 can be seen, and/or calculate the nearest distance between the fissures 70 and the tumor 92. Since tumors invading through the fissures have a significant effect on long-term survival, it is important to visualize the spatial relationship between fissures and tumors. In the example shown in FIG. 8, it can be seen that both tumors 92 are confined to a single lobe and they do not invade the fissures 70.

In addition, local and global measurement of fissure integrity can also be utilized to predict the spread of diseases such as cancerous tumors. Other measurements which may be made by the system in various embodiments include the distance between the fissures and anatomical landmarks or locations such as the lung apex, the diaphragm, and the ribs, for example. In addition, these measurements can be performed at different levels of lung inflation, to provide information about, and to help better understand, lung mechanics in both normal and diseased lungs.

As discussed above, the fissures are the interface between the lobes of the lungs and they are lined by the pleura. An analysis of the fissures can therefore include characterization of the pleura itself. For example, pleural thickening can occur in certain disease conditions, and in some cases is due to inflammation. Such pleural thickening can result in changes in the intensity distributions and thickness of fissure surface. For example, portions of the fissure may have an abnormal intensity on volumetric imaging which may be indicative of the presence of disease or fluid. Various embodiments may therefore identify the intensity, such as in Hounsfield Units (HU), of the fissures and of the various portions of the fissures if the intensity is not uniform. Various embodiments may therefore provide measurements of the intensity distribution and the thickness of the pleura, or can assist a clinician in making these measurements, to provide further information about and characterization of the associated disease.

In some embodiments, the shape of the fissure may be determined by the system. Fissure shape can be changed due to lung disease, such as emphysema. Thus, analysis of fissure shape can also be useful in characterizing lung disease. The shape analysis may include, but is not limited to, principal component analysis and surface curvature measurement, for example. These results may be provided in comparison to normal results, for example, to help identify areas of abnormality since the normal shape can be altered due to some diseases.

In some embodiments, the topology of the fissure surface may be characterized. The topological information may include, for example, the number of holes (incomplete portions) in the fissure, which could be caused by or associated with a vein crossing the fissure.

Figure 9:
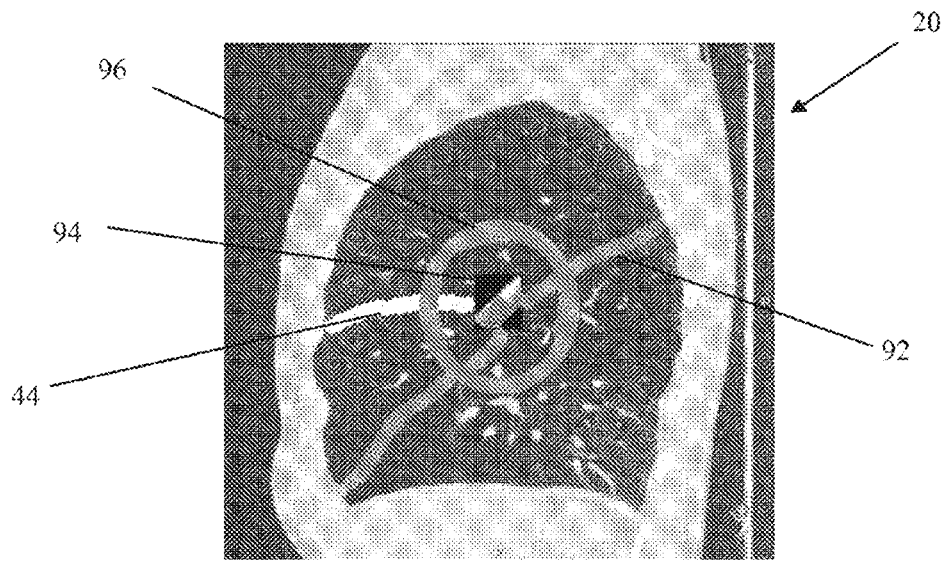
FIG. 9 illustrates a fissure editing tool in use to revise the identification of a portion of a fissure as complete or incomplete on a CT image.

In some embodiments, a clinician may interact with the visual display to identify the fissures manually or to edit the fissures that were automatically identified by the system. An example of an editing tool icon 94 is shown in FIG. 9, in which a sagittal CT image 20 of the lungs is shown. The editing tool 94 can be used to edit the enhanced fissure line 22, such as to change the characterization of the identified fissure from existing fissure 42 to incomplete fissure 44 or vice versa. The editing tool, the icon for which may appear differently from that shown in FIG. 9, may allow a user to change the identification of the voxels at the fissure location, relabeling them as either existing fissure or incomplete/missing fissure.

In some embodiments, the process of editing a fissure using a fissure editing tool may include the following steps. First, a user may select a fissure editing tool for use in a two-dimensional image. The two-dimensional image may include identification of the fissure locations as existing or incomplete, as automatically identified by the system, which may be shown enhancing the fissure by using colors such as blue for existing and green for missing fissure. The user may then position to the editing tool icon at a selected a location in the two-dimensional image including the automatically identified existing and missing fissure. The user may then direct the system to change the fissure identification (from existing to incomplete, or from complete to existing) using the tool. For example, the user may click and drag a mouse to move the corresponding tool icon on the display, at the location of the portion of the fissure for which the user wishes to change the fissure identification. During use, the tool editing icon may appear in a color matching the color of the new (revised) state of the fissure, such as a first color or shade of gray such as light gray for intact or a second color or shade of gray such as dark gray for missing fissure, for better visualization of the underlying CT data. The fissure label (existing or missing) in the edited image and neighboring images will be automatically updated according to the size of the 3D sphere. An example of this is shown in FIG. 9 in which circle 96 represents the central cross-section of the 3-dimensional volume within which the fissure identification will be changed, if so directed by the user. The color change may occur immediately while the user is interacting with the image, or may occur when the user indicates that editing is complete, such as by unclicking the mouse.

Figure 10:
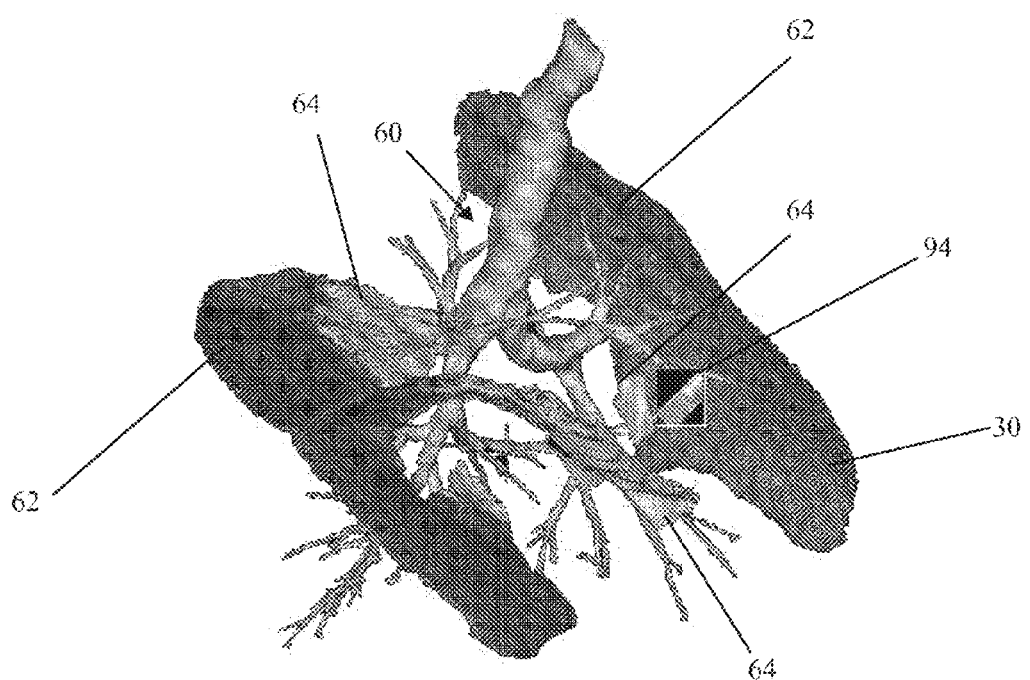
FIG. 10 illustrates a fissure editing tool in use to revise the identification of a portion of a fissure as complete or incomplete on a three-dimensional model of the fissure.

Fissure editing may also be performed by a user by interacting with a three-dimensional model of the fissures produced by the system. An example of this is shown in FIG. 10, in which the editing tool icon 94 is shown in the 3D model of the fissures 30. The model also includes a 3D model of the airway tree 60. The user may edit the fissure characterization using the following steps. First, the user may select the editing tool for use in the three-dimensional model, which displays both existing and incomplete portions 62, 64 of the fissures as automatically identified by the system and/or previously edited by a user. The user may place the editing tool icon 94 on a selected location on the fissure model 30. The user may then apply the tool to the fissure to change the identification of the fissure location as existing or incomplete, such as by clicking and dragging the icon using a mouse, at the fissure location as described above for editing the two-dimensional image. In response, the system may change the fissure characterization, and likewise change the fissure color shown in the model 30, to indicate the revised fissure characterization.

The use of the pulmonary visualization system which includes automatic lobar fissure identification, visualization, and characterization as described herein provides several advantages. The system may provide a priori knowledge to predict the response of a patient to a bronchoscopically-guided procedure such as an BLVR procedure. It may also provide an easily recognizable visual display of completeness and incompleteness of the lobar fissure, such as through the use of color coding. It may also provide an easily recognizable visual display of the spatial relationships between fissures and normal and abnormal lung structures including the airway tree, the lobes, the sub-lobes, the fissures, regions of emphysema, and tumors, for example. In addition, it may detect and identify normal and abnormal regions of the lungs and fissures and link two-dimensional data and images to multidimensional visualization and measurements. In some embodiments, it may offer "on-demand" measurement of fissures for purpose of immediate evaluation of normal and diseased states, determination of the appropriateness of a proposed procedure, and procedure planning. The automation of the measurement of the fissure integrity may provide enhanced clinical utility by allowing easier, faster, and more accurate decisions, thereby saving time, money and potentially lives.

Various embodiments may be used by physicians to predict the response of a patient with emphysema or other lung disease to a proposed procedure, such as the implantation of a device or other BLVR treatment. Treatment planning and determination of the most appropriate device therapy may be optimized by predicting response. For example, thoracic surgeons may use the information for treatment planning for lung volume reduction surgery. Radiologists and pulmonary clinicians may use these characterizations to determine the appropriate patients to triage to endobronchial BLVR therapy. Pulmonary clinicians may use the information to plan procedures for BLVR therapies and to evaluate treatment response.

In the foregoing detailed description, the invention has been described with reference to specific embodiments. However, it may be appreciated that various modifications and changes can be made without departing from the scope of the invention.

The invention claimed is:

1. A system for visualizing pulmonary fissures of a person's lungs comprising;
    a processor;
    software comprising instructions for the processor for creating a visual display comprising a two-dimensional model of the pulmonary fissures,
    wherein creating a visual display comprising the two-dimensional model of the pulmonary fissures comprises:
        accessing volumetric imaging data of the person's lungs;
        analyzing the volumetric imaging data to segment the lungs into lobes;
        using the segmented lobes, identifying locations at which pulmonary fissures should be present as the locations where the lobes abut each other;
        analyzing the volumetric images to identify locations at which pulmonary fissures are present as existing fissure;
        comparing the identified locations at which pulmonary fissures should be present to the identified locations at which pulmonary fissures are present to identify locations of missing fissure; and
        creating a visual display comprising the two-dimensional model of the pulmonary fissures comprising existing fissure portions and missing fissure portions, wherein the existing fissure portions are visually distinct from the missing fissure portions.

2. The system of claim 1 wherein the existing fissure portions are displayed in a different color than the missing fissure portions in the two-dimensional model of the pulmonary fissures.

3. The system of claim 2 wherein the software further comprises instructions to create a graphical user interface allowing a user to reclassify a location on the two-dimensional model of the pulmonary fissures from existing to missing or from missing to existing by interacting with the two-dimensional model of the pulmonary fissures on the graphical user interface.

4. The system of claim 2 wherein the two-dimensional model of the pulmonary fissures further comprises a two-dimensional representation of the lung parenchyma in combination with the fissures.

5. The system of claim 2 wherein the two-dimensional model of the pulmonary fissures further comprises a two-dimensional representation of a tumor in combination with the fissures, wherein the software further comprises instructions for identifying a location of the tumor by analyzing the volumetric imaging data.

6. The system of claim 5 wherein the software further includes instructions to calculate a distance between the tumor and a nearest fissure location.

7. The system of claim 1 wherein the software further comprises instructions for calculating a numerical value representing integrity of the fissures.

8. The system of claim 7 wherein the numerical value provides a relative proportion of amount of the fissures that is existing and amount of the fissures that is missing.

9. The system of claim 7 wherein the software further comprises instructions for calculating a numerical value representing integrity of a portion of a fissure abutting a lobe, wherein the portion of the fissure abutting the lobe is less than all of the fissure.

10. The system of claim 7 wherein the software further comprises instructions for calculating a numerical value representing integrity of a portion of a fissure abutting a sub-lobe.

11. The system of claim 1 wherein the software further comprises instructions for receiving directions from a user to reclassify a fissure location identified by the system as existing fissure to be identified and displayed as missing fissure in the two-dimensional model of the pulmonary fissures.

12. A system for visualizing pulmonary fissures of a patient's lungs comprising;
  a processor;
  software comprising instructions for the processor for creating a visual display comprising a two-dimensional model of the pulmonary fissures,
  wherein creating a visual display comprising the two-dimensional model of the pulmonary fissures comprises:
    accessing volumetric imaging data of the patient's lungs;
    analyzing the volumetric imaging data to segment the lungs into lobes and sub-lobes;
    using the segmented lobes, identifying locations at which pulmonary fissures should be present where the lobes abut each other;
    analyzing the volumetric images to identify locations at which pulmonary fissures are present;
    comparing the identified locations at which pulmonary fissures should be present to the identified locations at which pulmonary fissures are present to identify locations of missing fissure;
    identifying portions of the present and missing fissures which abut the sub-lobes; and
    creating a visual display comprising the two-dimensional model of the pulmonary fissures comprising existing fissure portions and missing fissure portions, wherein the existing fissure portions are visually distinct from the missing fissure portions and wherein the portions of the missing and existing fissures abutting the sub-lobes are visually distinct from each other.

13. The system of claim 12 wherein the existing fissure portions are displayed in a different color than the missing fissure portions in the two-dimensional model of the pulmonary fissures.

14. The system of claim 12 wherein the portions of the missing and existing fissures abutting the sub-lobes are each presented in a different color.

15. The system of claim 12 wherein the software further comprises instructions for calculating a numerical value representing integrity of the fissures, wherein the numerical value provides a relative proportion of amount of the fissures that is existing and amount of fissure that is missing.

16. The system of claim 15 wherein the numerical value representing integrity of the fissures is a calculation for the integrity of an entire fissure, of only a portion abutting a lobe, or only a portion of a fissure abutting a sub-lobe, wherein selection of the entire fissure, the portion abutting the lobe, or the portion abutting a sub-lobe can be determined by a user.

17. The system of claim 12 wherein the software further comprises instructions for receiving directions from a user interacting with the two-dimensional model of the pulmonary fissures on a graphical user interface to reclassify a fissure location identified by the system as existing fissure to be identified and displayed as missing fissure, and to reclassify a fissure location identified by the system as missing fissure to be identified and displayed as existing fissure.

18. A method for creating a two-dimensional model of pulmonary fissures of a patient comprising:
  accessing volumetric imaging data of the patient's lungs;
  analyzing the volumetric imaging data to segment the lungs into lobes;
  using the segmented lobes, identifying locations at which pulmonary fissures should be present as the locations where the lobes about each other;
  analyzing the volumetric images to identify locations at which pulmonary fissures are present as existing fissure;
  comparing the identified locations at which pulmonary fissures should be present to the identified locations at which pulmonary fissures are present to identify locations of missing fissure; and
  displaying the two-dimensional model of the pulmonary fissures on a display, wherein the visual display comprises existing fissure portions and missing fissure portions, wherein the existing fissure portions are visually distinct from the missing fissure portions.

19. The method of claim 18 further comprising calculating a numerical value representing integrity of the fissures, wherein the numerical value provides a relative proportion of amount of the fissures that is existing and amount of fissure that is missing.

20. The method of claim 18 further comprising receiving directions from a user interacting with the two-dimensional model of the pulmonary fissures to reclassify a fissure location identified by the system as existing fissure to be identified and displayed as missing fissure, and to reclassify a fissure location identified by the system as missing fissure to be identified and displayed as existing fissure.

* * * * *